United States Patent [19]

Fleig et al.

[11] 4,140,692
[45] Feb. 20, 1979

[54] MANUFACTURE OF 3-AMINO-1,2-BENZISOTHIAZOLES

[75] Inventors: Helmut Fleig, Mannheim; Helmut Hagen, Frankenthal, both of Fed. Rep. of Germany

[73] Assignee: BASF Aktiengesellschaft, Ludwigshafen, Fed. Rep. of Germany

[21] Appl. No.: 768,051

[22] Filed: Feb. 14, 1977

[30] Foreign Application Priority Data

Mar. 10, 1976 [DE] Fed. Rep. of Germany ....... 2609864

[51] Int. Cl.$^2$ .................. C07D 275/02; C07D 275/04
[52] U.S. Cl. ................................. 260/304 A; 424/270
[58] Field of Search ..................................... 260/304 A

[56] References Cited

U.S. PATENT DOCUMENTS

| 3,254,094 | 5/1966 | Ross | 260/304 A |
| 3,682,941 | 8/1972 | Becke et al. | 260/304 A |
| 3,787,572 | 1/1974 | Boshagen | 260/304 A |

Primary Examiner—Donald G. Daus
Assistant Examiner—Lisa Jones
Attorney, Agent, or Firm—Keil & Witherspoon

[57] ABSTRACT

3-Amino-1,2-benzisothiazoles are manufactured by reacting o-halobenzonitriles with ammonia and elementary sulfur. The products are fungicides and starting materials for the manufacture of dyes, crop protection agents and pharmaceuticals.

10 Claims, No Drawings

MANUFACTURE OF 3-AMINO-1,2-BENZISOTHIAZOLES

The present invention relates to a process for the manufacture of 3-amino-1,2-benzisothiazoles by reacting o-halo-benzonitriles with ammonia and elementary sulfur.

Angewandte Chemie, 36 (1923), 159, and Berichte der deutschen Chemischen Gesellschaft, 58 (1925), 2,095, disclose the reaction of thionaphthene-2,3-dione with ammonia and hydrogen peroxide to give 3-carbamyl-1,2-benzisothiazole and the conversion of the latter to 1,2-benzisothiazole by hydrolysis and decarboxylation. Berichte der deutschen Chemischen Gesellschaft, 56 (1923), 1,630, and Liebigs Annalen der Chemie, 454 (1927), 264, disclose the reaction of 2-formyl-4-nitrophenylsulfenyl bromide with ammonia to give 5-nitro-1,2-benzisothiazole. Benzisothiazoles can also be synthesized by cyclizing o-mercapto-phenyl-carbonyl compounds in the presence of polyphosphoric acid (Annali di Chimica, 53 (1963), No. 5, 577–587). German Laid-Open Application DOS No. 1,670,196 discloses the reaction of dihalomethylaryl compounds with ammonia and sulfur to give benzisothiazoles.

3-Amino-1,2-benzisothiazoles have hitherto been manufactured by other methods, since they differ in structure from the above benzisothiazoles. U.S. pat. No. 3,692,795 described a reaction of compounds of the formula

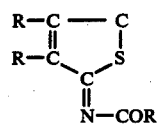

with hydroxylamine in the presence of organic solvents at an elevated temperature, followed by hydrolysis of the resulting N-acyl-3-amino-1,2-benzisothiazoles in the presence of excess acid at the reflux temperature, treatment of the reaction mixture with alkali and extraction of the end product with, for example, ether. 3-Amino-1,2-benzisothiazole has also been prepared, using a 5-stage synthesis (Berichte der deutschen Chemischen Gesellschaft, 58 (1925), 2,095), using thionaphthene-2,3-dione, a compound difficult to obtain, as the starting material; the reaction stages comprise the manufacture of 3-carbamyl-1,2-benzisothiazole by reacting the thionaphthene-2,3-dione with ammonia and hydrogen peroxide, manufacture of the hydrazide, azide and urethane and, finally, decomposition to give 3-amino-benzisothiazole.

All these processes are unsatisfactory as regards easy accessibility of starting materials, economics and simplicity of operation, coupled with better yield of end product.

We have found that 3-amino-1,2-benzisothiazole of the formula

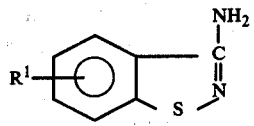

where $R^1$ is hydrogen, an aliphatic or cycloaliphatic radical, an aromatic radical which may or may not be fused, halogen, alkoxy, nitro or

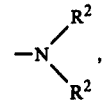

where the individual $R^2$'s are identical or different and each is hydrogen or an aliphatic, cycloaliphatic, araliphatic or aromatic radical, are obtained in an advantageous manner when o-halobenzonitriles of the formula

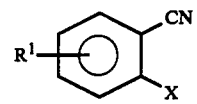

where X is halogen and $R^1$ has the above meanings, are reacted with ammonia and elementary sulfur.

In the case of the reaction of 2-chlorobenzonitrile with ammonia and sulfur, the reaction can be represented by the following equation:

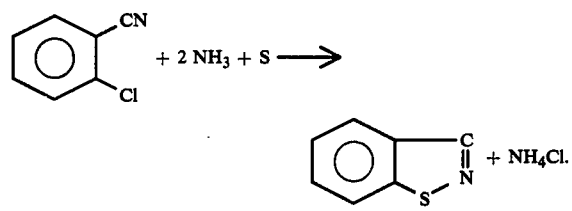

Compared to conventional processes, the process of the invention uses more easily accessible starting materials and gives 3-amino-1,2-benzisothiazoles more simply and more economically, in better yield and greater purity. These advantageous results are surprising in view of the prior art.

Preferred starting materials II and, accordingly, preferred 3-amino-1,2-benzisothiazoles I are those where $R^1$ is alkyl of 1 to 6 carbon atoms which may or may not be substituted by amino, cycloalkyl of 5 to 12 carbon atoms, phenyl or naphthyl, both of which may or may not be fused, fused naphthoquinon-1,4-ylene, hydrogen, bromine or especially chlorine, alkoxy of 1 to 4 carbon atoms, nitro or

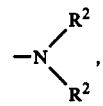

where the individual $R^2$'s may be identical or different and each is hydrogen, alkyl of 1 to 6 carbon atoms, alkenyl of 3 to 6 carbon atoms, cycloalkyl of 5 to 8 carbon atoms, aralkyl of 7 to 12 carbon atoms or phenyl. The above radicals may in addition be substituted by groups which are inert under the reaction conditions, eg. alkyl or alkoxy, each of 1 to 4 carbon atoms, nitro or amino. The starting materials II, ammonia and elementary sulfur may be used in about stoichiometric amounts, but a ratio of from 2 to 10 moles of ammonia and/or of from 0.9 to 1.1 gram atoms of sulfur per mole of starting material II is preferred.

Examples of suitable starting materials II are: 5-nitro-, 4-dimethylamino-, 4-diethylamino-, 5-diethylamino-, 4-diallylamino-, 4-di-(2'-methallyl)-amino-, 6-methyl-, 3-ethyl-, 5-hexyl-, 6-isobutyl-, 5-propyl-, 4-tert.-butyl-, 4-cyclohexyl-, 4-cyclopentyl-, 5-phenyl-, 4-phenyl-, 4-nitrophenyl-, 4-p-toluyl-, 4-p-ethoxyphenyl-, 4-naphthyl-, 4-bromo-, 5-ethoxy-, 6-methoxy-, 6-dicyclohexylamino-,4-dibenzylamino-, 4-diphenylamino- and 4-p-xylyl-2-chlorobenzonitrile; 2-chlorobenzonitrile and 2-bromobenzonitrile; 1-chloro-2-cyano-, 2-chloro-3-cyano- and 2-chloro-1-cyano-naphthalene; 1-chloro-2-cyano-, 2-chloro-3-cyano and 2-chloro-1-cyano-anthraquinone; 1-chloro-2-cyano-, 2-chloro-3-cyano- and 2-chloro-1-cyano-anthracene; 1-chloro-2-cyano-, 2-chloro-3-cyano- and 2-chloro-1-cyano-phenanthrene; and appropriately substituted bromoarylnitriles.

The reaction is as a rule carried out at from 20° to 250° C., advantageously from 60° to 250° C. and preferably from 100° to 200° C., under atmospheric or superatmospheric pressure, continuously or batchwise. This reaction pressure is in general due to the total vapor pressure of the components at the reaction temperature. If appropriate, organic solvents which are inert under the reaction conditions may be used, examples being alkanols and cycloalkanols, eg. ethanol, n-butanol, isobutanol, methylglycol, cyclohexanol, propanol, methanol, isopropanol, sec.-butanol, tert.-butanol and 2-ethylhexanol, ethers, eg. ethyl propyl ether, diisobutyl ether, methyl tert.-butyl ether, n-butyl ethyl ether, di-n-butyl ether, dioxane, diisoamyl ether, diisopropyl ether, anisole, phenetole, cyclohexyl methyl ether, diethyl ether, tetrahydrofuran and thioanisole and, preferably, glycol ethers, eg. methylglycol or ethylglycol, and mixtures of the above. Advantageously, the amount of solvent used is from 200 to 10,000 percent by weight, preferably from 300 to 1,000 percent by weight, based on starting material II.

The reaction may be carried out as follows: the starting material II, elementary sulfur and ammonia are reacted with one another, in the presence or absence of a solvent, in a pressure reactor for from 3 to 15 hours at the above temperature. The 1,2-benzisothiazole I is obtained from the reaction mixture in accordance with the conventional processes, eg. by filtration, distillation and, if appropriate, washing the residue with, for example, acetone, filtering, concentrating the filtrate and then recrystallizing the residue from a suitable solvent, eg. toluene.

The compounds which may be manufactured by the process of the invention are fungicides and valuable starting materials for the manufacture of dyes, crop protection agents and pharmaceuticals. As regards their use, reference may be made to the publications cited above and to U.S. Pat. No. 3,787,572, issued Jan. 22, 1974.

In the Examples which follow, parts are by weight and bear the same relation to parts by volume as that of the kilogram to the liter.

EXAMPLE 1

137.5 parts of o-chlorobenzonitrile, 32 parts of sulfur and 150 parts of ammonia in 500 parts of methylglycol are kept for 10 hours in a pressure vessel at 160° C. and 25 bars. After the reaction has ended, the ammonium chloride which has precipitated is filtered off and the solvent is evaporated; acetone is added to the residue and the ammonium chloride which has precipitated is filtered off. The residue left after concentrating the acetone solution is recrystallized from toluene. 95 parts of 3-amino-1,2-benzisothiazole (63% of theory), having a melting point of 113 – 114° C., are obtained.

EXAMPLE 2

37.5 parts of 1-chloro-2-naphthonitrile, 6.4 parts of sulfur and 40 parts of ammonia in 500 parts of methylglycol are heated at 160° C. for 10 hours in a pressure vessel under 20 bars. After evaporating off the solvent, acetone is added to the residue. The ammonium chloride which has precipitated is filtered off and the residue obtained after evaporating off the acetone is recrystallized from toluene. Yield, 29 parts (72% of theory) of 3-aminonaphtho-[2,1-d]-isothiazole, having a melting point of 172° C.

We claim:

1. A process for the manufacture of 3-amino-1,2-benzisothiazoles of the formula

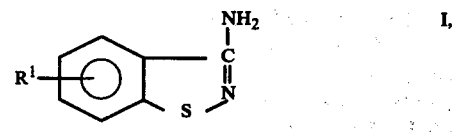

where $R^1$ is hydrogen, alkyl of 1 to 6 carbon atoms; said alkyl substituted by amino; cycloakyl of 5 to 12 carbon atoms; phenyl; napthyl; naphthoquinon-1,4-ylene; alkoxy of 1 to 4 carbon atoms; or

where the individual $R^2$'s may be identical or different and each is hydrogen, alkyl of 1 to 6 carbon atoms, alkenyl of 3 to 6 carbon atoms, cycloalkyl of 5 to 8 carbon atoms, aralkyl of 7 to 12 carbon atoms or phenyl; one of said radicals substituted by alkyl of 1 to 4 carbon atoms, alkoxy of 1 to 4 carbon atoms, nitro or amino; chlorine, bromine; or nitro; or

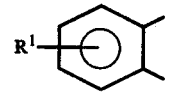

represents a divalent radical of napththalene, anthraquinone, anthracene, or phenanthrene in which o-halobenzonitriles of the formula

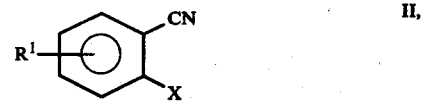

where X is halogen and $R^1$ has the above meanings, are reacted with ammonia and elementary sulfur.

2. A process as claimed in claim 1, wherein the reaction is carried out with from 2 to 10 moles of ammonia and/or from 0.9 to 1.1 gram atom of sulfur per mole of starting material II.

3. A process as claimed in claim 1, wherein the reaction is carried out at from 20° to 250° C.

4. A process as claimed in claim 1, wherein the reaction is carried out at from 60° to 250° C.

5. A process as claimed in claim 1, wherein the reaction is carried out at from 100° to 200° C.

6. A process as claimed in claim 1, wherein the reaction is carried out in organic solvents which are inert under the reaction conditions.

7. A process as claimed in claim 1 wherein said o-halobenzonitrile is 2-chloronitrile; 2-bromonitrile; a 2-chlorobenzonitrile bearing as a substituent one of the groups 5-nitro-, 4-dimethylamino-, 4-diethylamino-, 5-diethylamino-, 4-diallylamino-, 4-di-(2'-methallyl)-amino-, 6-methyl-, 3-ethyl-, 5-hexyl-, 6-isobutyl-, 5-propyl-, 4-tert.-butyl-, 4-cyclohexyl-, 4-cyclopentyl-, 5-phenyl-, 4-nitrophenyl-, 4-p-toluyl-, 4-p-ethoxyphenyl-, 4-naphthyl-, 4-bromo-, 5-ethoxy-, 6-methoxy-, 6-dicyclohexylamino-, 4-dibenzylamino-, 4-diphenylamino- or 4-p-xylyl; 1-chloro-2-cyano-, 2-chloro-3-cyano- or 2-chloro-1-cyano-naphthalene; 1-chloro-2-cyano-, 2-chloro-3-cyano or 2-chloro-1-cyano-anthraquinone; 1-chloro-2-cyano-, 2-chloro-3-cyano- or 2-chloro-1-cyano-anthracene; or 1-chloro-2-cyano-, 2-chloro-3-cyano- or 2-chloro-1-cyano-phenanthrene.

8. A process as claimed in claim 1 wherein said o-halobenzonitrile is 2-chlorobenzonitrile.

9. A process as claimed in claim 1 wherein said o-halobenzonitrile is 1-chloro-2-naphthonitrile.

10. 3-Amino-naphth-isothiazole of the formula

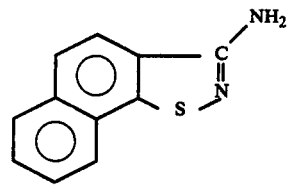

* * * * *